United States Patent [19]

Thiele et al.

[11] 4,153,803
[45] May 8, 1979

[54] CHOLESTEROL-LOWERING PHENOXYALKANOIC ACID ESTERS

[75] Inventors: Kurt Thiele, Zofingen; Quazi Ahmed, Strengelbach; Rudolf Adrian, Vordemwald; Ulrich Jahn, Zofingen, all of Switzerland

[73] Assignee: Siegfried Aktiengesellschaft, Zofingen, Switzerland

[21] Appl. No.: 773,144

[22] Filed: Mar. 1, 1977

Related U.S. Application Data

[63] Continuation-in-part of Ser. No. 536,120, Dec. 24, 1974, abandoned.

[30] Foreign Application Priority Data

Dec. 27, 1973 [CH] Switzerland ............... 18144/73
Mar. 28, 1974 [CH] Switzerland ............... 4355/74
Nov. 18, 1974 [CH] Switzerland ............... 15329/74
Nov. 18, 1974 [CH] Switzerland ............... 15330/74

[51] Int. Cl.² ................................. C07C 69/76
[52] U.S. Cl. ........................ 560/57; 544/264; 544/271; 544/335; 546/222; 260/325 R; 260/559 B; 260/559 T; 560/9; 560/17; 560/58; 560/61; 560/62; 560/63; 562/426; 562/431; 562/468; 562/471; 562/472; 424/308; 424/317; 424/324
[58] Field of Search ............... 560/57, 58; 260/520 C

[56] References Cited

U.S. PATENT DOCUMENTS

| | | | |
|---|---|---|---|
| 3,262,850 | 7/1966 | Jones et al. | 560/57 |
| 3,332,842 | 7/1967 | Bencze | 560/57 |
| 3,332,957 | 7/1967 | Bencze | 560/58 |
| 3,362,997 | 1/1968 | Bolhofer | 560/62 |
| 3,716,583 | 2/1973 | Nakamura et al. | 260/520 |

FOREIGN PATENT DOCUMENTS

| | | | |
|---|---|---|---|
| 2356655 | 5/1974 | Fed. Rep. of Germany | 560/62 |
| 705251 | 10/1954 | United Kingdom | 560/62 |

OTHER PUBLICATIONS

Miyoshi et al., J. Pharm. Soc. Japan, 94 (9) 1061–1069 (1974).

*Primary Examiner*—Jane S. Myers
*Attorney, Agent, or Firm*—Finnegan, Henderson, Farabow & Garrett

[57] ABSTRACT

Compounds possessing pharmaceutical activity as substances able to lower the level of fatty substances in the blood possess the following general formula:

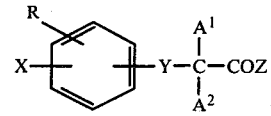

wherein R represents hydrogen, halogen, hydroxy or alkyl or alkoxy containing from 1 to 4 carbon atoms;
$A^1$ and $A^2$ which can be the same or different are hydrogen or alkyl containing from 1 to 9 carbon atoms such that $A^1$ and $A^2$ contain together not more than 10 carbon atoms,
Y is oxygen, in which case X is benzyl, benzyloxy or benzylthio or benzyl, benzyloxy or benzylthio substituted by R and Z is amine, azacyclohydrocarbyloxy cycloalkoxy containing from 3 to 6 ring carbon atoms or tertiary aminoalkoxy or pivaloyloxyalkoxy in which the alkoxy group contains from 1 to 3 carbon atoms, or X is hydrogen and Z is pivaloyloxyalkoxy in which the alkoxy group contains from 1 to 3 carbon atoms, or
Y is oxygen, X is benzyl, benzyloxy or benzylthio or benzyl, benzyloxy or benzylthio substituted by R and Z is alkoxy containing from 1 to 4 carbon atoms, hydroxy or $O^-M^+$, M being a metal cation of Main Groups I, II or III of the Periodic System of the Elements or an organic base cation or ammonium ion, $A^1$ and $A^2$ being the same and being as aforesaid or being different with one of $A^1$ and $A^2$ being hydrogen or both being hydrogen and X being a para substituent with respect to Y in the benzene ring in the same general formula,
Y is oxygen, X is hydrogen and Z is amine, azacyclohydrocarbyloxy or pivaloyloxyalkoxy in which the alkoxy group contains from 1 to 3 carbon atoms,
or Y is sulphur, in which case X is hydrogen, benzyl, benzyloxy or benzylthio or benzyl, benzyloxy or benzylthio substituted by R and Z is amine, azacyclohydrocarbyloxy, alkoxy containing from 1 to 4 carbon atoms, hydroxy, $O^-M^+$ wherein M is a metal cation of Main Groups I, II or III of the Periodic System of The Elements or an organic base cation or ammonium ion, cycloalkoxy containing from 3 to 6 ring carbon atoms or tertiaryaminoalkoxy, pivaloyloxyalkoxy or pyridyl-C-alkoxy in which the alkoxy group contains from 1 to 3 carbon atoms, and pharmacologically acceptable acid addition and quaternary ammonium salts of compounds containing basic groups, and optical isomers of said compounds when $A^1$ and $A^2$ are different.

5 Claims, No Drawings

CHOLESTEROL-LOWERING PHENOXYALKANOIC ACID ESTERS

This application is a continuation-in-part of our co-pending Application Ser. No. 536,120 filed Dec. 24th, 1974, now abandoned.

This invention relates to novel benzylphenoxyalkanoic acids and esters and salts thereof, to methods for the preparation thereof, to pharmaceutical compositions comprising the same and to the use of the compounds in reducing cholesterol and triglyceride levels in blood.

Aryloxy carboxylic acid esters have been proposed for use in the therapy of excessive cholesterol and triglyceride levels in the blood in British Patent specification No. 860,303. One of the substances described in British Patent specification No. 860,303, namely the methyl ester of 2-(4'-chlorophenoxy)-isobutyric acid having the short name "Clofibrat" as recommended by World Health Organisation, has so far acquired considerable importance in the clinical treatment of human beings. It has since been found that many new compounds of related structure are superior to Clofibrat in their cholesterol-reducing effect to a surprisingly high extent. Phenoxy-alkanoic acids and esters thereof of such type are described, for example, in U.S. Pat. Nos. 3,546,273 filed 1st June, 1967 and 3,948,973 which is a continuation-in-part of Ser. No. 284,577 filed Aug. 29th, 1972. Compounds of similar structure, but to which no hypocholesterol emic or hypolipemic effect has been attributed are described in U.S. Pat. No. 3,474,095 and British Patent specification No. 705,251. Finally, certain benzylphenoxy alkanoic acids and esters thereof effective in the therapy of excessive cholesterol and triglyceride levels in the blood have been described by F. Miyoshi, H. Fukami and Y. Sakao in J. Pharm. Soc. Japan 94 (9) 1061-1069 (1974) and in German Offenlegungsschrift No. 2,356,655, which documents constitute prior art in respect of some of the compounds to be described specifically hereinafter.

Compounds according to the present invention possessing hypocholesterolemic and hypolipemic activity greater than mentioned in any prior art documents applicable thereto possess the general formula:

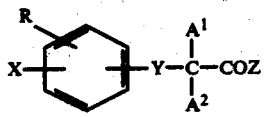

wherein R represents hydrogen, halogen, hydroxy or alkyl or alkoxy containing from 1 to 4 carbon atoms;

$A^1$ and $A^2$ which can be the same or different are hydrogen or alkyl containing from 1 to 9 carbon atoms such that $A^1$ and $A^2$ contain together not more than 10 carbon atoms, Y is oxygen, in which case X is benzyl, benzyloxy or benzylthio or benzyl, benzyloxy or benzylthio substituted by R and Z is amine, azacyclohydrocarbyloxy, cycloalkoxy containing from 3 to 6 ring carbon atoms or tertiary aminoalkoxy or pivaloyloxyalkoxy in which the alkoxy group contains from 1 to 3 carbon atoms, or X is hydrogen and Z is pivaloyloxyalkoxy in which the alkoxy group contains from 1 to 3 carbon atoms, or Y is oxygen, X is benzyl, benzyloxy or benzylthio or benzyl, benzyloxy or benzylthio substituted by R and Z is alkoxy containing from 1 to 4 carbon atoms, hydroxy or $O^-M^+$, M being a metal cation of Main Groups I, II or III of the Periodic System of the Elements or an organic base cation or ammonium ion, $A^1$ and $A^2$ being the same and being as aforesaid or being different with one of $A^1$ and $A^2$ being hydrogen or both being hydrogen and X being a para substituent with respect to Y in the benzene ring in the same general formula, Y is oxygen, X is hydrogen and Z is amine, azacyclohydrocarbyloxy or pivaloyloxyalkoxy in which the alkoxy group contains from 1 to 3 carbon atoms, or Y is sulphur, in which case X is hydrogen, benzyl, benzyloxy or benzylthio or benzyl, benzyloxy or benzylthio substituted by R and Z is amine, azacyclohydrocarbyloxy, alkoxy containing from 1 to 4 carbon atoms, hydroxy, $O^-M^+$ wherein M is a metal cation of Main Groups I, II or III of the Periodic System of The Elements or an organic base cation or ammonium ion, cycloalkoxy containing from 3 to 6 ring carbon atoms or tertiaryaminoalkoxy, pivaloyloxyalkoxy or pyridyl-C-alkoxy in which the alkoxy group contains from 1 to 3 carbon atoms, and pharmacologically acceptable acid addition and quaternary ammonium salts of compounds containing basic groups, and optical isomers of said compounds when $A^1$ and $A^2$ are different.

This invention also provides a process for the production of a compound according to the present invention wherein a phenol of the general formula

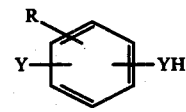

wherein X, R and Y have the aforesaid meanings, or a corresponding alkali metal or alkaline earth metal phenolate or triphenolate is reacted with a compound of the general formula

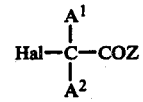

in which Hal is a halogen atom and $A^1$, $A^2$ and Z have the meanings set out hereinabove, and recovering the said compound, the compounds (II) and (III) being selected to yield a compound according to this invention.

In an alternative process for the production of compounds according to the present invention, a phenol or thiophenol of the aforesaid general formula II or a corresponding alkali metal or alkaline earth metal phenolate of thiophenolate is reacted in the presence of an at least trihalogenated methane derivative and in the presence of a strong base with a ketone of formula $A^1$-CO-$A^2$ in which $A^1$ and $A^2$ have the meanings set out hereinabove and, depending on the nature of Z in the aforesaid general formula I (a) if necessary esterifying, either as such or as a reactive derivative thereof, a carboxyl group in the reaction product so obtained or obtained by alkaline hydrolysis of a reaction product so obtained, with a hydroxy-terminated compound Z'-OH wherein Z' has a meaning as given aforesaid for Z with the exclusion of amine, hydroxyl or $O^-M^+$ or reacting said carboxyl group with an amine, ammonia or a base or salt containing a said cation $M^+$; or (b) when the reaction product of the compound of general formula (II), the trihalogenated methane derivative and the ketone contains an alkoxy carbonyl group, subjecting the reaction product to ester exchange or to aminolysis with ammonia or an amine to yield a product respectively containing a said group -O-Z' or a group Z", in which Z" is an amino group, the various reactants employed in the reaction sequence being such as to produce compounds according to the present invention.

As previously indicated, with compounds according to the invention, the substituent R can be, inter alia, halogen. The halogen may be fluorine, chlorine, bromine or iodine, but is preferably chlorine. Of particular interest are compounds in which X is benzyl, benzyloxy or benzylthio and R is a 4'-chloro atom. R may also be alkyl or alkoxy containing from 1 to 4 carbon atoms, more particularly methyl, ethyl, n-propyl or isopropyl or one of the butyl isomers, or methoxy, ethoxy, n-propoxy or isopropoxy or one of the butoxy isomers. When R is a substituent in the benzene ring of a phenoxy or thiophenoxy group in the compounds of general formula I, it may be in the ortho or meta position with regard to Y. In such a case, R is preferably an alkyl or alkoxy group as aforesaid.

As previously indicated, with certain of the compounds according to the invention, $A^1$ and $A^2$ may be different so that the carbon atom linking $A^1$ and $A^2$ is asymetric. For this purpose, two groups $A^1$ and $A^2$ are to differ in their carbon atom content such that the total carbon atom content of the two alkyl groups is not more than 10. Thus $A^1$ and $A^2$ can be methyl, ethyl, n-propyl or isopropyl, n-butyl isobutyl or t-butyl or any of the pentyl, hexyl, heptyl, octyl or nonyl groups. The alkyl groups preferably contain from 1 to 4 carbon atoms. The nature of the optical isomerism based on the carbon atom linking the ether oxygen atom and the carboxyl group is not critical. Both D- and L- forms of the compounds as well as racemates thereof possess hypocholesterolemic and hypolipemic activity.

Compounds of the present invention may be free acids or bases or salts thereof.

Thus, the compounds may contain a cation $M^+$ which can be an alkaline earth metal, for example sodium, potassium or lithium, an alkaline earth metal, for example magnesium, calcium, strontium or barium or a metal of the third main group of the Periodic System of the Elements, in particular aluminium. Insofar as $M^+$ may be designated by a polyvalent cation, it should be appreciated that what is in fact meant here is $\frac{1}{2} M^{++}$ or $\frac{1}{3} M^{+++}$ depending upon the valency of the metal M.M May may also be a cation of an organic base or ammonia. Examples of such cations are piperidinium, methylthiazolidinium, morpholinium, diethyl-hydroxyethyl ammonium, diethylammonium, diethanol ammonium and ammonium.

Insofar as Z may be basic in nature, a compound of the invention containing such a radical Z may be isolated in the form of a pharmacologically acceptable acid addition or quaternary ammonium salt. Such acid addition salts can be derived from a variety of organic and inorganic acids, such as sulphuric, phosphoric, hydrochloric, hydrobromic, hydroiodic, sulphamic, citric, lactic, oleic, succinic, tartaric, cinnamic, acetic, benzoic, gluconic, ascorbic and related acids. Similarly, the quaternary ammonium salts can be derived from a variety of organic esters of sulphuric, hydrohalic and aromatic sulphonic acids. Amongst such esters are methyl chloride and bromide, ethyl chloride, propyl chloride, butyl chloride, isobutyl chloride, benzyl chloride and bromide, phenethyl bromide, naphthylethyl bromide, dimethyl sulphate, ethylbenzene sulphonate, ethyltoluene sulphonate, ethylene chlorohydrin, propylene chlorohydrin, methallyl bromide and crotyl bromide.

Insofar as compounds according to the present invention may be of a basic nature, such basicity may derive from three sources.

Firstly Z in the aforesaid general formula I may be pyridyl-C-alkoxy in which case the compounds of the invention possess the general formula IV

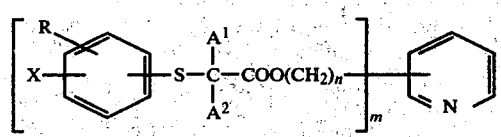

wherein R, X, $A^1$ and $A^2$ have the aforesaid meanings, n is an integer of 1 to 3, preferably being equal to 1, and m is 1 or 2. Insofar as m may be equal to 2, it should be appreciated that in the aforesaid general formula I, the group Z is intended to be denoted by the radical of formula

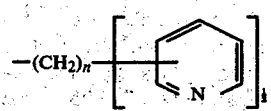

V

When m is 1, the pyridine group may be substituted in the 2, 3 or 4-position, although substitution is preferably in the 3-position. When m is 2, the pyridine ring may be substituted in any combination of positions, for example 2, 3- 2,4-, 2,6- or 3,4-. 2,6-substitution is preferred.

A second way in which basicity may be introduced into the compound of formula I is when Z is a tertiary amino alkoxy group. The alkoxy part of the group may contain 1 to 3 carbon atoms and preferably contains 2 carbon atoms. The tertiary amino group may be a dialkyl amino group in which the alkyl radicals contain from 1 to 4 carbon atoms, being methyl, ethyl, a propyl isomer or a butyl isomer. Of particular interest are compounds in which the tertiary amino group possesses the general formula

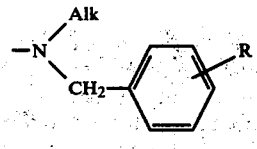

VI wherein Alk is an alkyl radical containing from 1 to 4 carbon atoms and R has the aforesaid meaning. Radicals Z of this type, of particularly preferred nature, are N-methyl-N-benzyl-aminoethoxy groups.

The tertiary amino group of a tertiary amino alkoxy group Z may also be of a cyclic nature, possibly being heteroaromatic. Examples of compounds providing the tertiary amine nitrogen atom are compounds of purine and pyrimidine type including, in particular, theophylline.

A third way in which basicity may be introduced into compounds of the invention is if Z is an azacyclic hydrocarbyloxy group, that is a mono or polycyclic organic compound containing a ring nitrogen atom and substituted by a hydroxyl group whereby the compound is able to esterify a free acid constituted by a compound of general formula I wherein Z is hydroxyl. Examples of such azacyclic hydrocarbyloxy groups are N-methyl-piperidyl and 3-oxindolyl. Radicals Z of this type are exemplified by 4-(N-methyl)piperidoxy and 3-oxindoloxy.

A further characteristic type of group Z which may be present in compounds according to the present invention is pivaloyloxy alkoxy in which the alkoxy group contains from 1 to 3 carbon atoms. The alkoxy group may be methyl, ethyl, or propyl, but is preferably methyl. Furthermore, Z can be a cycloalkoxy group containing from 3 to 6 carbon atoms preferably cyclopentoxy. It can, however, also be cychexoxy, cyclobutoxy or cyclopropoxy.

As will be appreciated from the foregoing, two basic preparative methods have been found to be particularly satisfactory for use in the production of compounds according to the present invention.

In the first such method, a phenol or thiophenol is reacted with a compound of general formula III hereinabove. The halogen atom in the compound of the general formula III is preferably chlorine or bromine. Thus, for example, the compound 4-(4'-chlorobenzyl)-phenol can be condensed with the ethyl ester of 2-bromo-2-methylpropionic acid and the condensation product obtained can be subjected to a hydrolytic cleavage of the ethyl group to form 2-[4-(4'-chlorobenzyl)-phenoxy]-2-methyl propionic acid. The reaction sequence may be terminated at this stage or if a reaction product wherein Z is one of the more complex types of radical described above is to be obtained, this acid can be reacted with thionyl chloride to form its acid chloride which can be esterified by reaction with a hydroxy-substituted compound whose formula will depend upon the nature of the group Z which it is desired to introduce into the molecule. When the group Z is a tertiary amino alkoxy group, it may be more convenient to introduce the group Z into the molecule in two stages. Thus when esterification of the acid chloride is effected, a halo alcohol will be used to yield a compound having a terminal halogen atom at which reaction can be effected with a compound, for example, a secondary amine, in order to enable a tertiary amino group terminated group compound to be obtained.

Although a multistage preparative process for a tertiary amino alkyl ester according to the present invention has been described in the preceding paragraph, it is possible to use in place of an ethyl ester as indicated in the specific example given, an ester of the formula B-OH where B is a group which when combined in the final product in a group B-OCO- provides a moiety B-O- constituting the group Z in the aforesaid general formula I.

In the second aforesaid process for the production of compounds according to the present invention, a phenol or thiophenol of general formula (II) is reacted with a ketone of formula $A^1$-CO-$A^2$, in the presence of an at least trihalogenated methane derivative. When the trihalogenated methane derivative is a simple halomethane, for example chloroform of carbontetrachloride, the reaction product will possess the general formula:

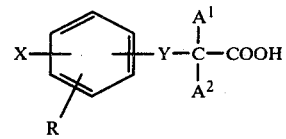

VII

When a substituted trihalogenated methane is used, the substituent will esterify the carboxyl group in the above formula. The product obtained in either case may be a compound according to the present invention for utilisation as such. Alternatively, it may be converted to a different compound falling within the scope of the aforesaid general formula I.

In one procedure, a carboxyl group in the reaction product so obtained or obtained by alkaline hydrolysis of a reaction product so obtained, can be esterified, after conversion to a reactive derivative thereof for example an acyl chloride obtained by reaction with for example thionyl chloride, with a hydroxy terminated compound B-OH in which the group B has a meaning as aforesaid. Alternatively, the carboxyl group or reactive derivative thereof can be reacted with ammonia or an amine to form an amide. Thus it is then possible to obtain compounds according to the present invention in which Z is a group of formula -N $R^3$ $R^4$ wherein $R^3$ and $R^4$ are hydrogen atoms or alkyl groups containing from 1 to 4 carbon atoms or are atoms which together with the nitrogen atom form a nitrogen-containing heterocyclic ring, for example, a pyrollidine, piperidine, piperazine, 4-methyl piperazine or morpholine ring. When $R^3$ and $R^4$ are alkyl, they are exemplified by methyl, ethyl, propyl isomers and butyl isomers.

In an alternative reaction sequence applicable in the case when the trihalogenated methane derivative reacted with the phenol or thiophenol in the presence of the ketone and a strong base which can be sodium or potassium hydroxide contains a fourth substituent which is not a halogen atom and the product contains an alkoxy carbonyl group, the product of the first stage contains an alkoxy carbonyl group. The reaction product can be subjected then to ester exchange with a corresponding ester or to aminolysis with ammonia or an amine depending upon the nature of the group Z in the final product.

Compounds of the general formula I hereinabove have been found to be particularly effective agents for lowering the cholesterol level of blood. Although, as mentioned above, aryloxycarboxylic esters have been proposed for use in the therapy of excessive cholesterol and triglyceride levels in the blood in for example British Patent specification No. 860,303, the compounds of the present invention are generally more effective.

Results of tests carried out on animals are set out in the following Table, these results having been obtained with a representative selection of compounds according to the present invention in comparison with Clofibrat. In the Table which follows, the various columns are given reference numerals which have the following meanings:

(1) Sets out identification numbers of test substances employed;

(2) Indicates the nature of the group:

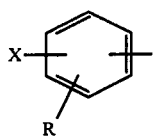

in the overall general formula I;

(3) Denotes the nature of Y;

(4) and (5) Denote the radicals $A^1$ and $A^2$ respectively in general formula I;

(6) Denotes the nature of the symbol "Z" in general formula I;

(7) Denotes the quantity of test substance in mg/kg of body weight of mouse which were orally administered to the test animals in tests to determine the actuate toxicity LD50 therefor;

(8) Shows the quantity of test substance in mg/kg of body weight of rat undergoing tests which were orally administered thereto to determine the daily dose which lowers the serum cholesterol level by 25% (ED25);

(9) These are therapeutic index value calculated from the numerical values of the two preceding columns, that is to say the ratio $LD50_{mouse}/ED25_{rat}$ ratio.

In column 2 the meanings of the symbols employed are as follows:

α = p-benzylphenyl
β = p-(p'-chlorobenzyl)-phenyl
γ = o-(p'-chlorobenzyl)-phenyl
δ = o-benzyl-p-chlorophenyl To determine the LD50 values, tests were carried out using male animals. After a single administration of the test substances, the animals were observed, their body weight being monitored, for at least seven days until toxic symptoms had faded. The volume of substances injected amounted to 10 ml/kg.

To determine the ED25 values set out in the Table male rats weighing 100–200 g were given the test substance once daily orally, emulsified in 3% gum arabic in a volume of 1 ml/100 g body weight. Administration was usually commenced on Monday and continued up to and including Thursday of a second week. The final treatment on the Thursday was given at about 16.00 hours. Then the rats, which throughout the experiment had been kept in dosage groups of 8–10 in size 3 Makrolon cages, were kept fasting. On the Friday morning, the animals were sacrificed by carotid section under ether narcosis. After centriguation of the blood obtained in this way, the total cholesterol content of the serum was determined on a Beckman or DBG spectrophotometer by the method of Richterich, R. (Clinical Chemistry, S. Karger,/New York 1965, p. 232). The average group values of the Table were compared with those from a simultaneously investigated control group.

In addition to possessing the strong hypocholesterol emic effect which can be seen from the Table, the compounds of the present invention also lower considerably the triglyceride content of the blood and are in this respect again several times better in their action than Clofibrat.

By way of example, hypertriglyceridaemia produced in rats by having fructose to their drinking water was lowered by Clofibrat administered in a dosage of 85 mg/kg by 25%. per oral administration, whereas when administering compound No. 24074 referred to in the Table, dosages of 5.6 mg/kg were sufficient to achieve the same effect.

Table

| (1) | (2) | (3) | (4) | (5) | (6) | (7) | (8) | (9) |
|-----|-----|-----|-----|-----|-----|-----|-----|-----|
| 6274 | β | O | H | H | OH | 2700 | 50 | 54 |
| 1374 | β | O | H | H | $OC_2H_5$ | 3000 | 25 | 120 |
| 18374 | β | O | H | H | O—⟨tetrahydrofuryl⟩ | >>3000 | 54 | >65 |
| 22974 | β | O | H | $CH_3$ | OH | 1700 | 29 | 59 |
| 2774 | β | O | H | $CH_3$ | $OC_2H_5$ | 2500 | 33 | 76 |
| 17474 | β | O | H | $C_2H_5$ | $OC_2H_5$ | >>3000 | 54 | >56 |
| 23074 | β | O | $CH_3$ | $CH_3$ | OH | 2400 | 47 | 51 |
| 8674 | β | O | $CH_3$ | $CH_3$ | $OC_2H_5$ | >>3000 | 25 | >120 |
| 25974 | β | O | $CH_3$ | $CH_3$ | O—⟨tetrahydrofuryl⟩ | >>3000 | 41 | >73 |
| 25674 | β | O | H | $CH_3$ | O—$(CH_2)_2$N($CH_3$)($CH_2$-Ph) | >3000 | 50 | >60 |
| 7274 | β | O | H | H | O—$(CH_2)_2$N($CH_3$)($CH_2$-Ph)·HCl | >>30000 | 66 | >45 |
| 25874 | β | O | $CH_3$ | $CH_3$ | O—$(CH_2)_2$N($CH_3$)($CH_2$-Ph) | >>3000 | 31 | >97 |

Table-continued

| (1) | (2) | (3) | (4) | (5) | (6) | (7) | (8) | (9) |
|---|---|---|---|---|---|---|---|---|
| 24874 | β | O | H | CH$_3$ | (piperidine structure: O—[ring]—N—CH$_3$) | 2700 | 28 | 96 |
| 28374 | β | O | CH$_3$ | CH$_3$ | (oxindole structure: O—CH—C(=O)—NH—phenyl) | >>3300 | >86 | >35 |
| 23174 | β | O | CH$_3$ | CH$_3$ | (O(CH$_2$)$_2$—N=CH—N... pyrimidine-dione with N—CH$_3$ groups) | >>3000 | 20 | >150 |
| 15174 | β | O | H | H | —OCH$_2$OCO—C(CH$_3$)$_3$ | >>3000 | 25 | >120 |
| 23574 | β | O | H | CH$_3$ | —OCH$_2$OCO—C(CH$_3$)$_3$ | >3000 | 17 | >176 |
| 24074 | β | O | CH$_3$ | CH$_3$ | —OCH$_2$OCO—C(CH$_3$)$_3$ | >>3000 | 15 | >200 |
| 28274 | β | O | CH$_3$ | C$_2$H$_5$ | —OCH$_2$OCO—C(CH$_3$)$_3$ | >>3000 | 21 | >163 |
| 27874 | β | O | H | H | —NH$_2$ | >>3000 | <25 | >>120 |
| 27774 | β | O | CH$_3$ | CH$_3$ | —NH$_2$ | >>3000 | 19 | >158 |
| 2874 | γ | O | H | CH$_3$ | —OC$_2$H$_5$ | >>3000 | >100 | >30 |
| 22074 | δ | O | H | H | —OC$_2$H$_5$ | >>3000 | 58 | >52 |
| 33275 | β | O | H | CH$_3$ | —OCH$_3$ | 2230 | 12 | 186 |
| 33174 | β | O | H | CH(CH$_3$)$_2$ | —OC$_2$H$_5$ | >>3000 | 15 | >>200 |
| 33274 | β | O | CH$_3$ | C$_2$H$_5$ | —OCH$_2$CH$_2$—N=CH—N... (pyrimidine-dione with N—CH$_3$ groups) | >>3000 | 27 | >111 |
| 37874 | β | S | CH$_3$ | C$_2$H$_5$ | OH | 2150 | >100 | <265 |
| 33375 | β | O | H | CH$_3$ | OCH(CH$_3$)$_2$ | 2900 | 38 | 76 |
| 8675 | α | O | CH$_3$ | C$_2$H$_5$ | NH$_2$ | >>3000 | >100 | >30 |
| 11875 | β | O | CH$_3$ | C$_2$H$_5$ | NH$_2$ . ½ n-hexane | >3000 | >300 | >10 |
| 11775 | β | O | CH$_3$ | (CH$_2$)$_2$CH$_3$ | NH$_2$ . ½ n-hexane | >3000 | >100 | >30 |

It will be appreciated that for therapeutic use, the compounds of the invention can be made up, in accordance with well known pharmaceutical techniques, into compositions having as an essential active ingredient a compound of the invention in association with a pharmaceutical carrier therefor. If desired, the compositions can be made up in a dosage unit form suitable for the particular mode of administration, the quantity of active ingredient in each dosage unit being such that one or more units are required for each therapeutic administration. The dosage unit may exist, for example, in the form of a tablet, sugar coated pill, capsule or packaged powder for oral administration, or in the form of a sterile injectable solution or suspension, if desired contained in an ampoule, for parenteral administration. The dosage unit preferably contains from 5 to 300 milligrams of active substance. The compounds of the present invention may also be incorporated in suspensions, emulsions or solutions for oral administration. For a person of average build, it is expected that a dosage of from 0.02 to 1.5 gram per day would be suitable for therapeutic purposes.

The following examples illustrate the invention. Although detailed examples only describe the preparation of a small number of compounds according to the present invention, further compounds have been prepared whose properties are summarised at the end of the examples.

EXAMPLE 1

4-(4'-chlorobenzyl)-phenoxyacetic acid ethyl ester 9.0 g (0.18 mol) of sodium hydride in the form of a 55 to 60% emulsion in mineral oil were introduced into 40 ml of dimethylformamide (DMF). To the mixture was slowly added a solution of 39.3 g (0.18 mol) of 4'-chloro-4-hydroxydiphenylmethane in 90 ml of DMF. The mixture as obtained was stirred for 15 minutes at 70° C., whereafter a solution of 30.0 g (0.18 mol of ethyl bromacetate in 90 ml of DMF was added and stirring took place for 7 hours at 130° C. The solvent was thereafter removed in a Buchi rotary evaporator. The residue was treated with water and then thoroughly extracted with dichloromethane. After being dried over magnesium sulphate, the extract was concentrated by evaporation under reduced pressure. After chromatography over 20 g of Al$_2$O$_3$, elution with 200 ml of benzene and distillation, the residue yielded 23.0 g of pure product, of boiling point 156°–160° C. (0.03 mm).

C$_{17}$H$_{17}$ClO$_3$ (304.8) Calculated: C 66.98 H 5.62 Cl 11.64: Found: C 66.51 H 5.80 Cl 11.85.

EXAMPLE 2

4-(4'-chlorobenzyl)-phenoxyacetic acid N-benzyl-N-methylaminoethyl ester hydrochloride A solution of 21.0 g (0.07 mol) of p-(p'-chlorobenzyl-phenoxyacetyl chloride in 140 ml of anhydrous xylene was added dropwise and while stirring to a solution of 11.55 g (0.07 mol) of N-benzyl-N-methyl-2-aminoethanol in 70 ml of anhydrous pyridine. The reaction mixture was heated for 24 hours at reflux temperature, whereupon the solvent was evaporated in a Büchi rotary evaporator under reduced pressure; the residue was taken up in 10% aqueous $KHCO_3$ solution and extracted with dichloromethane. The organic phase was washed with water and dried over anhydrous magnesium sulphate. 27.0 g of brown resin were obtained therefrom by evaporation. This resin was dissolved in benzene and filtered over 35.0 g of $Al_2O_3$. By combining the three first fractions, each of 50 ml, and concentrating by evaporation, 25.0 g of a light brown resin were obtained. After dissolving in ether and adding ethereal hydrogen chloride, solid hydrochloride precipitated after trituration. Recrystallisation from acetone/ether yielded 13.0 g of product in the form of lustrous white crystals of melting point 120°-122° C.

$C_{25}H_{26}ClNO_3 \cdot HCl$ (460.3): Calculated: C 65.22 H 5.91 N 3.04 Cl 15.40: Found: C 65.41 H 5.96 N 3.20 Cl 15.68.

EXAMPLE 3

4-(4'-chlorobenzyl)-phenoxyacetic acid 4-(N-methyl)-piperidyl ester hydrochloride A solution of 6.0 g (0.02 mol) of p-(p'-chlorobenzyl)-phenoxyacetyl chloride in 40 ml of anhydrous xylene was added as in Example 2 to a solution of 2.30 g (0.02 mol) of 4-hydroxy-N-methylpiperidine in 20 ml of anhydrous pyridine, whereafter the mixture was kept at reflux temperature for 24 hours while stirring. Working up in the same way as in Example 2 and filtration of the solution in benzene through 10 g of $Al_2O_3$ yielded 8.5 g of brown resin, and this resin, after being dissolved in ether and after addition of HCl/ether, could be caused to solidify by trituration. The crude hydrochloride (5.8 g) was dissolved in acetone and boiled for 3 minutes with active carbon. By recrystallisation from acetone/ether, 3.5 g of hydrochloride were obtained with a melting point of 170°-171° C.

$C_{21}H_{24}ClNO_3 \cdot HCl$ (410.3): Calculated: C 61.47 H 6.14 N 3.41 Cl 17.28: Found: C 61.36 H 6.14 N 3.43 Cl 17.54.

EXAMPLE 4

4-(4'-chlorobenzyl)-phenoxyacetic acid 2-(7-theophyllinyl) ethyl ester

A solution of 6.0 g (0.02 mol) of p-(p'-chlorobenzyl)-phenoxy-acetyl chloride in 50 ml of anhydrous xylene was added to a solution of 4.48 g (0.02 mol) of 7-(β-hydroxyethyl)-theophylline in 25 ml of anhydrous pyridine. The mixture was heated for 20 hours while stirring to reflux temperature and the residue was worked up as in the preceding Examples 2 to 5. Crystallisation from dichloromethane/methanol yielded 6.5 g of product in the form of white lustrous needles of melting point 134°-135° C.

$C_{24}H_{23}ClN_4O_5$ (482.9): Calculated: C 59.69 H 4.80 N 11.60 Cl 7.34: Found: C 59.35 H 4.97 N 11.51 Cl 7.84.

EXAMPLE 5

2-Methyl-2-[4-(4'-chlorobenzyl)-phenoxy]-butyric acid 2-(7-theophyllinyl) ethyl ester

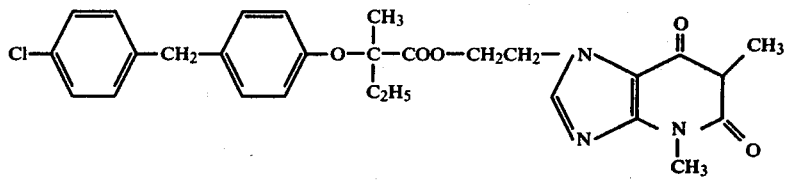

29 g (0.086 mol) of 2-methyl-2-[4-(4'-chlorobenzyl)-phenoxy]-butyryl chloride are dissolved in 200 ml of anhydrous xylene and 50 ml of anhydrous pyridine and a solution of 19.35 g (0.086 mol) of 7-(2-hydroxyethyl)-theophylline in 50 ml of anhydrous xylene and 50 ml of anhydrous pyridine is added. The mixture is heated for 24 hours and while stirring at reflux temperature and is thereafter concentrated by evaporation in a Büchi rotary evaporator. The residue is extracted with dichloromethane, and the organic phase is washed with water, dried over $MgSO_4$ and concentrated by evaporation under reduced pressure. The solid residue which is thereby obtained yields 28.5 g of product of melting point 105°-106° C. after being recrystallised from methanol.

$C_{27}H_{29}ClN_4O_5$ (525.0): Calculated: C 61.77 H 5.57 N 10.67 O 15.24 Cl 6.75: Found: C 61.83 H 5.59 N 10.57 O 15.15 Cl 6.94.

EXAMPLE 6

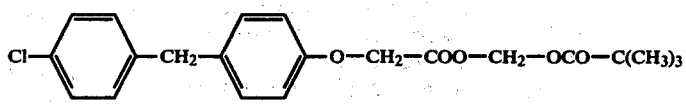

4-(4'-Chlorobenzyl)-phenoxy acetic acid-(pivaloyloxymethyl)ester

To a solution of 8.3 g (0.06 mol) of 4-(4'-chlorobenzyl)-phenoxy acetic acid in 50 ml of dimethylformamide are added 6.0 g (0.06 mol) of triethylamine, whereafter the mixture is stirred for 30 minutes at room temperature and, after adding 9.0 (0.06 mol) of chloromethyl pivalate, is heated for 6 hours in an oil bath at 85°-90° C. The residue which is obtained by concentration by evaporation at reduced pressure in a Büchi rotary evaporator is washed with water and extracted with ether. The ethereal solution is once again washed with water, dried over anhydrous magnesium sulphate and concentrated by evaporation in the Büchi rotary evaporator, an oil being obtained which quickly solidifies. By recrystallisation from ether/n-hexane, 9.5 g of product are obtained in the form of white crystals with the melting point 54°-55° C.

$C_{21}H_{23}ClO_5$ (390.8): Calculated: C 64.53 H 5.93 Cl 9.07: Found: C 64.57 H 5.88 Cl 9.67.

EXAMPLE 7

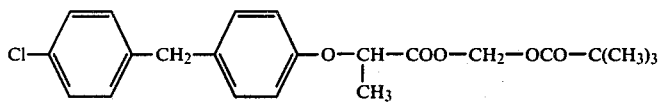

2-[4-(4'-Chlorobenzyl)-phenoxy]-propionic acid-(pivaloyloxymethyl)-ester

To a solution of 43.5 g (0.15 mol) of α-[p-(p'-chlorobenzyl)-phenoxy]-propionic acid in 250 ml of dimethylformamide are added 30.0 g (0.3 mol) of triethylamine and, after stirring for half an hour at room temperature, 45.0 g (0.3 mol) of chloromethyl pivalate. The reaction mixture is heated in the oil bath for 6 hours at 90° C. and is thereafter worked up in accordance with the procedure described in Example 14, there being obtained 50.0 g of white needles which, on recrystallisation from n-hexane, once again produce white needles of melting point 65° C.

$C_{22}H_{25}ClO_5$ (404.8): Calculated: C 65.26 H 6.22 Cl 8.76: Found: C 65.27 H 6.23 Cl 8.29.

EXAMPLE 8

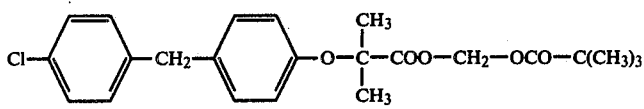

2-[4-(4'-Chlorobenzyl)-phenoxy]-isobutyric acid-(pivaloyloxymethyl)-ester

To a solution of 27.4 g (0.09 mol) of p-(p'-chlorobenzyl) phenoxyisobutyric acid in 150 ml of dimethylformamide are added 18.0 g (0.18 mol) of triethylamine and, after stirring for half an hour at room temperature, 27.0 g (0.18 mol) of chloromethyl pivalate are added. After heating for 6 hours at 90° C. and working up in the manner indicated in the preceding examples, a liquid is obtained which, after distillation, yields 26.0 g of a light yellow liquid product; boiling point 204°-209° C./0.02 mm Hg.

$C_{23}H_{27}ClO_5$ (418.9): Calculated C 65.94 H 6.50 Cl 8.46: Found: C 66.34 H 6.56 Cl 8.42.

The α-[4-(4-chlorobenzyl)-phenoxy]-α-methylbutyric acid-(pivaloyloxymethyl)-ester, obtained by a similar procedure, using α-[p-(p'-chlorobenzyl)phenoxy]-α-methylbutyric acid shows a boiling point of 213°-214° C./0.01 mm Hg.

EXAMPLE 9

2-Methyl-2-[4-(4'-chlorobenzyl)-phenylmercapto]-butyric acid

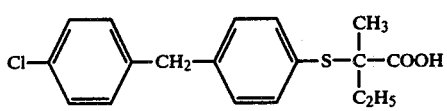

3.1 g of sodium hydride (60% suspension in oil) are suspended in 60 ml of dimethylformamide (DMF). A solution of 11.8 g of 4-(4'-chlorobenzyl)-thiophenol in 12 ml of DMF is then slowly added dropwise and while stirring, the mixture becoming heated. After continuing stirring for 1 hour, a solution of 15.7 g of 2-bromo-2-methyl-butyric acid ethyl ester in 16 ml of DMF is added dropwise and stirring is continued for another 2 hours at 70° C. The solvent is then distilled off under reduced pressure. The residue is treated with normal NaOH and the insoluble ester is extracted with ether. Concentration of the ethereal solution by evaporation provides a crude yield of 17.7 g (97.5%). The 2-methyl-2-[4-(4'-chlorobenzyl)-phenylmercapto]-butyric acid ethyl ester thus obtained as intermediate product is boiled for 1 hour under reflux in the unpurified state and for the purpose of saponification with 25 ml of methanolic KOH solution (25%) for 1 hour further. The solvent is then distilled off and the residue is dissolved in water and treated with active carbon. After filtration, acidification is carried out with dilute hydrochloric acid and extraction is effected with ether. The residue concentrated by evaporation yields 13.7 g of crude product (80%), from which the pure acid of melting point 88°-89° C. is obtained after recrystallisation from petroleum ether.

$C_{18}H_{19}ClO_2S$ (334.9): Calculated: C 64.56 H 5.72 O 9.55 Cl 10.59 S 9.58: Found: C 64.69 H 5.44 O 9.44 Cl 10.61 S 9.50.

EXAMPLE 10

2-Methyl-2-[p-(p'-clorobenzyl)]butyramide

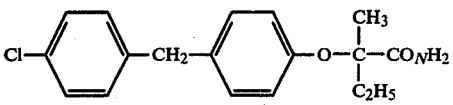

Ammonia gas was bubbled into a solution of dl-2-methyl-2-[p-(p'-chlorobenzyl)phenoxy]-butyryl chloride (50 g) in 500 ml dried ether for ½ hour. The reaction mixture was treated several times with water, dried over anhydrous magnesium sulphate and the organic layer was evaporated in vacuo. The resulting residue was purified by column chromatography in a column containing 200 g of neutral alumina using n-hexane as the eluant. The colourless oil thus obtained in a yield of 40.0 g showed one spot when subjected to silica gel thin layer chromatography.

$C_{18}H_{20}ClNO_2 \cdot \frac{1}{4}$n-hexane (339.35): Calculated: C 69.01 H 6.98 N 4.13 Cl 10.45: Found: C 69.36 H 6.98 N 3.69 Cl 10.50.

EXAMPLE 11

2-[p-(p'-chlorobenzyl)phenoxy]acetamide

The prcoedure of Example 10 was repeated using, however, as acid chloride starting material 21.08 g of [4-(4'-chlorobenzyl)phenoxy]acetylchloride. The corresponding amide was obtained which when crystallised from dichloromethane gave shiny white crystals of melting point 133°-134° C.

$C_{15}H_{14}ClNO_2$ (275.7): Calculated: C 65.34 H 5.12 N 5.08 Cl 12.86: Found: C 65.36 H 5.13 N 4.78 Cl 13.17.

EXAMPLE 12

2-Methyl-2-[p-(p'-chlorobenzyl)phenoxy]propionamide

The procedure of Example 10 was again repeated using on this occasion as acid chloride starting material 20.0 g of 2-methyl-2-[p-(p'-chlorobenzyl)phenoxy]propionylchloride. The corresponding amide was obtained which was crystallised from dichloromethane as white crystals of melting point 95°–96° C.

$C_{17}H_{18}ClNO_2$ (303.80): Calculated: C 67.21 H 5.97 N 4.61 Cl 11.67: Found: C 67.42 H 6.03 N 4.31 Cl 11.87.

Additional compounds which have been prepared by procedures referred to in the foregoing Examples were in compounds having a group Z in general formula I of white type were prepared, were as follows:

I—Methyl-2-[4-(4'-chlorobenzyl)phenoxy]propionate
II—Ethyl 2-isopropyl-2-[p-(p'-chlorobenzyl)phenoxy-]acetate
III—Isopropyl 2-[p-(p'-clorobenzyl)phenoxy]propionate
IV—2-methyl-2-(4-benzylphenoxy)butyramide.

We claim:

1. A compound of the formula

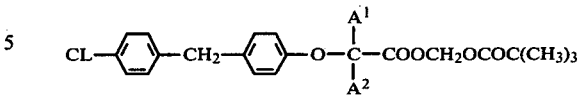

wherein $A^1$ and $A^2$ are individually selected from the group consisting of hydrogen and $C_1$–$C_4$ alkyl.

2. A compound according to claim 1, which is pivaloyloxymethyl p-(p'-chlorobenzyl)phenoxyacetate.

3. A compound according to claim 1, which is pivaloyloxymethyl 2-[p-(p'-chlorobenzyl)phenoxy]propionate.

4. A compound according to claim 1, which is pivaloyloxymethyl 2-methyl-2-[p-(p'chlorobenzyl)phenoxy]propionate.

5. A compound according to claim 1, which is pivaloyloxymethyl 2-methyl-2-[p-(p'-chlorobenzyl)phenoxy]butyrate.